(12) United States Patent
Noda

(10) Patent No.: US 6,620,637 B2
(45) Date of Patent: Sep. 16, 2003

(54) SEMICONDUCTOR ANALYSIS APPARATUS, SEMICONDUCTOR ANALYSIS METHOD AND METHOD FOR MANUFACTURING SEMICONDUCTOR DEVICE

(75) Inventor: Takafumi Noda, Sakata (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 10/147,342

(22) Filed: May 16, 2002

(65) Prior Publication Data

US 2003/0002035 A1 Jan. 2, 2003

(30) Foreign Application Priority Data

Jun. 27, 2001 (JP) ........................................ 2001-194429

(51) Int. Cl.[7] ............................................... G01B 31/26
(52) U.S. Cl. ............................................................ 438/14
(58) Field of Search .......................... 438/14; 445/1.24; 356/301

(56) References Cited

U.S. PATENT DOCUMENTS 4,856,897 A * 8/1989 Fateley ........................ 356/301
5,853,310 A * 12/1998 Nishimura ................... 445/1.24

OTHER PUBLICATIONS

Raman Microprobe Analysis of patterned T1–2212 Thin Films; Kirsten Myers, Jun. 1997; IEEE Transactions on Applied Superconductivity; p. 2126 through 2129.*

* cited by examiner

Primary Examiner—John F. Niebling
Assistant Examiner—Andre C Stevenson
(74) Attorney, Agent, or Firm—Harness, Dickey & Pierce, P.L.C.

(57) ABSTRACT

In a semiconductor analysis method in accordance with the present invention, a semiconductor integrated circuit defining an object to be measured is put in an operating state, a laser beam is irradiated on the object to be measured, scattered light of the irradiated laser beam scattered on the object to be measured is spectroscopically separated by a Raman spectroscopy apparatus, amounts of shifts in Raman spectra appearing due to the Raman effect are calculated, temperature of minute areas of the object to be measured is calculated based on the relation between the temperature obtained in advance and the amounts of frequency shifts, and the defective location that is generating heat is detected based on the temperature.

1 Claim, 2 Drawing Sheets

SEMICONDUCTOR ANALYSIS APPARATUS, SEMICONDUCTOR ANALYSIS METHOD AND METHOD FOR MANUFACTURING SEMICONDUCTOR DEVICE

BACKGROUND OF THE INVENTION

1. Technical Field of the Invention

The present invention relates to a semiconductor analysis apparatus, a semiconductor analysis method and a method for manufacturing a semiconductor device, in which a minute defective location can be accurately determined by using a Raman spectroscopic analysis.

2. Discussion of Related Art

FIG. 2 shows a block diagram of a conventional semiconductor analysis apparatus. The semiconductor analysis apparatus is used for a method for analyzing defects in semiconductor devices using a liquid crystal analysis. The liquid crystal analysis is an analysis method using a polarizing phenomenon of the liquid crystal.

A device to be measured 101 defining an object to be measured is a semiconductor integrated circuit apparatus in a state in which circuits are completed on a semiconductor wafer. To observe the internal state of the semiconductor integrated circuit apparatus to analyze defects therein, liquid crystal is thinly coated on its surface, and the liquid crystal is heated up to about a polarizing temperature. Then, it is placed in a measurement apparatus that is similar to a semiconductor wafer prober, and probes are abutted against bonding pads thereof to achieve electrical connection. Operation voltages and input signals that operate the internal circuits are supplied through the probes from a tester 105 that is composed of a pattern generation circuit 102, an oscillation circuit 103 and a control circuit 104.

A TV camera 106 photographs the entire area of at least one semiconductor integrated circuit or the entire area of circuits to be focused on the surface of the device to be measured 101. To photograph the device to be measured 101, the camera 106 is provided with a lens system that magnifies and photographs the surface of the device.

As well known, the refractive index of liquid crystal is temperature dependent. In the mean time, wirings and elements on the device to be measured generate heat according to currents that circulate therein. Accordingly, the refractive index of liquid crystal coated on the surface changes according to the wirings and elements in which currents circulate, and they appear as a pattern. In other words, an image photographed by the camera has a pattern corresponding to the wiring and element pattern in which current circulates.

A signal of the image photographed by the camera is converted by a data converter 107 into two-digit pattern data and inputted in a computer 108.

The computer 108 is provided with circuit-logic information 109 and layout information 110 being as expected values, examines the circuit logic information according to inputted conditions given by the tester 105, and forms pattern information of the passages and elements in which current should circulate based on the layout information. The pattern information is compared with the actual pattern obtained by the data conversion described above to thereby analyze presence or absence of defects.

In other words, by coating liquid crystal on a wafer and heating the liquid crystal adjacent to a polarizing temperature, and specifying defective locations that generate heat upon circulating current in the semiconductor integrated circuit, a defect analysis is conducted. Defective locations that can be concretely specified by the semiconductor analysis apparatus are those defective potions caused by metal short-circuits and defective locations having a higher resistance than a designed value. These defective locations involve greater heat generation than the normal case. Therefore, they can be specified as defective locations.

In the conventional semiconductor analysis apparatus described above uses liquid crystal that is harmful to the human body, and the liquid crystal is carcinogenic material. In addition, since the polarizing area of liquid crystal spreads widely, it is difficult to narrow down a spot for detecting a defective location to a minute area. This is becoming a greater problem as the miniaturization of the design rule is further progressed. In other words, it is difficult to accurately specify a minute defective location in a semiconductor integrated circuit apparatus that is greatly miniaturized.

On the other hand, there is a hot electron analysis that takes a shorter analyzing time. However, the hot electron analysis can only be applied to objects that accompany light emission of hot electrons, and thus cannot specify defects involving short circuits.

The present invention is made in view of the circumstances described above, and its object is to provide a semiconductor analysis apparatus, a semiconductor analysis method and a method for manufacturing a semiconductor device, in which a minute defective location can be accurately determined.

SUMMARY OF THE INVENTION

To solve the problems described above, a semiconductor analysis apparatus in accordance with the present invention is characterized in comprising:

- a laser oscillator that emits a Raman laser beam and a pattern taking laser beam for taking a pattern image of an object to be measured;
- a stage for mounting an object to be measured onto which the Raman laser beam and the pattern taking laser emitted from the laser oscillator are irradiated;
- a Raman spectroscopy apparatus that takes out to spectroscopically separate scattered light from the object to be measured onto which the Raman laser beam is irradiated, and detects Raman spectra obtained;
- a camera that receives reflected light from the object to be measured onto which the pattern taking laser beam is irradiated to obtain a pattern image of the object to be measured; and
- a computer that combines data of the Raman spectra detected by the Raman spectroscopy apparatus and data of the pattern image obtained by the camera, to thereby judge a temperature of a fine region in the pattern of the object to be measured.

A semiconductor analysis method in accordance with the present invention is characterized in comprising:

- setting a semiconductor integrated circuit defining an object to be measured in an operating state;
- irradiating a Raman laser beam and a pattern taking laser beam on the object to be measured;
- receiving reflected light of the irradiated pattern taking laser beam reflected on the object to be measured by a camera and detecting a pattern image from data of the received light;
- spectroscopically separating with a Raman spectroscopy apparatus scattered light of the irradiated Raman laser beam scattered on the object to be measured, and detecting Raman spectra obtained;

combining data of the Raman spectra and data of the pattern image, to thereby judge a temperature of a fine region in the pattern of the object to be measured; and detecting from the temperature a defective location that generates heat.

By the semiconductor analysis method described above, a defective location is specified by detecting heat that is generated at the defective location by using a Raman spectrum shift. In this type of Raman spectroscopic analysis, Raman spectrum shifts are sensitive to temperatures of an object to be measured. Therefore, it can specify a defective location such as a subtle metal short-circuit defect to a degree that can be barely specified by a scanning electron microscope (SEM), and is capable of analyzing a spot region of up to 0.2 µm. Therefore, a defective area such as a metal short-circuit can be narrowed down to a fine region in a short time. In particular, defective locations can be readily and accurately specified even when miniaturization of the design rule is further advanced.

A method for manufacturing a semiconductor device in accordance with the present invention is characterized in comprising:

a step of preparing an object to be measured; and a step of analyzing a defective location in the object to be measured, wherein the step of analyzing comprises:

setting a semiconductor integrated circuit defining the object to be measured in an operating state;

irradiating a Raman laser beam and a pattern taking laser beam on the object to be measured;

receiving reflected light of the irradiated pattern taking laser beam reflected on the object to be measured by a camera and detecting a pattern image from data of the received light;

spectroscopically separating with a Raman spectroscopy apparatus scattered light of the irradiated Raman laser beam scattered on the object to be measured, and detecting Raman spectra obtained;

combining data of the Raman spectra and data of the pattern image, to thereby judge a temperature of a fine region in the pattern of the object to be measured; and detecting from the temperature a defective location that generates heat.

Also, in the method for manufacturing a semiconductor device in accordance with the present invention, the step of preparing an object to be measured may be the step of preparing a semiconductor wafer in which a semiconductor integrated circuit is formed in a completed state or an IC chip.

DETAILED DESCRIPTION OF THE PREFERRED EMBODIMENTS OF THE PRESENT INVENTION

Embodiments of the present invention will be described below with reference to the accompanying drawings.

Figure 1:
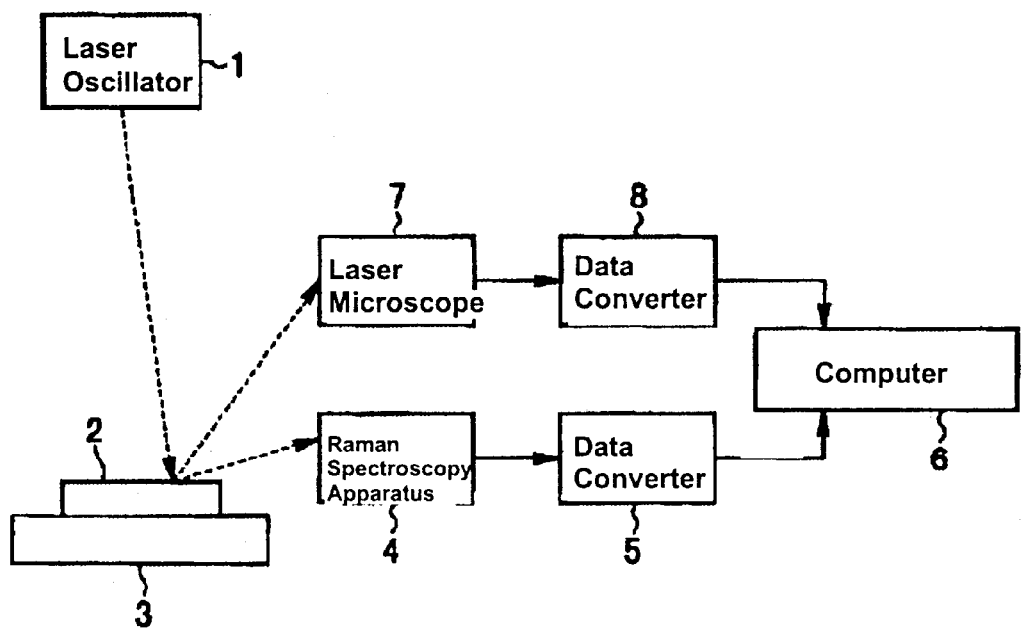
FIG. 1 schematically shows a structure of a semiconductor analysis apparatus in accordance with an embodiment of the present invention.
Figure 2:
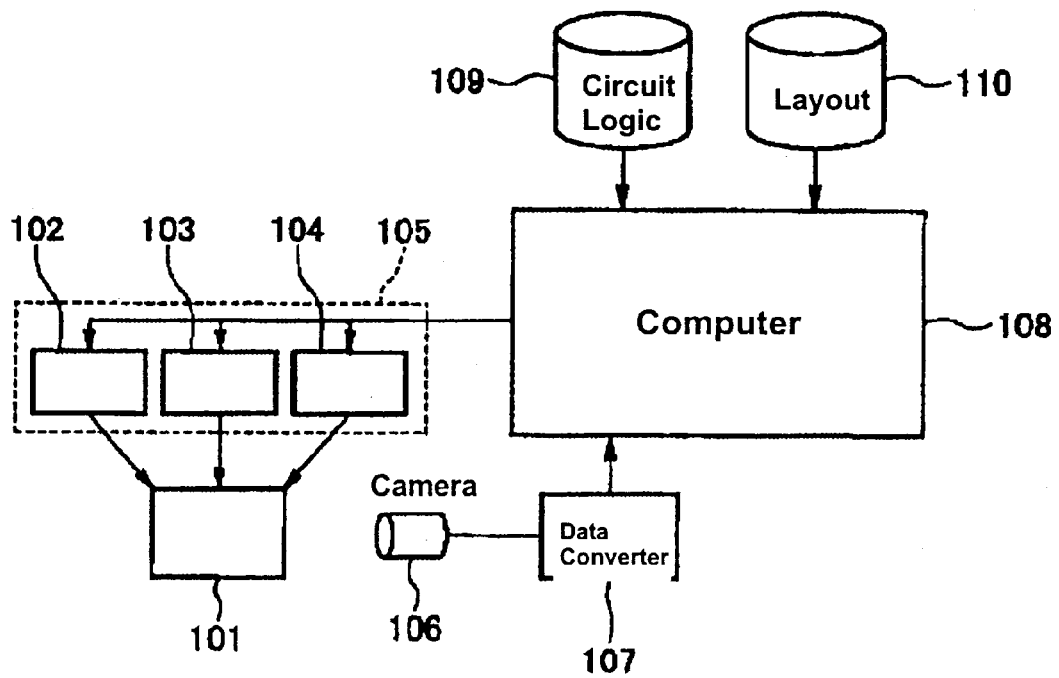
FIG. 2 shows a block diagram of a conventional semiconductor analysis apparatus.

FIG. 1 schematically shows a structure of a semiconductor analysis apparatus in accordance with an embodiment of the present invention. The semiconductor analysis apparatus uses the principle of laser Raman spectroscopy, and uses Raman spectrum shift to measure temperature of minute areas in a semiconductor wafer to thereby specify minute defective locations.

The semiconductor analysis apparatus is formed from a laser oscillator 1 that emits laser beams, a stage 3 for mounting thereon a semiconductor wafer (or IC chip) 2 defining an object to be analyzed, a Raman spectroscopy apparatus 4, a data converter 5, a laser microscope 7, a data converter 8 and a computer 6. Semiconductor integrated circuits in a completed form are formed on the semiconductor wafer 2.

The laser oscillator 1 is structured such that it can emit a Raman laser and a laser for taking a wafer pattern (chip pattern) image. Also, as the laser oscillator 1 irradiates the semiconductor wafer 2 with the Raman laser beam, the Raman spectroscopy apparatus 4 takes out and spectroscopically separates scattered light scattered on the semiconductor wafer 2, and detects a shifted position of a specified peak value of the obtained Raman spectrum.

As the laser oscillator 1 irradiates the semiconductor wafer 2 with the wafer pattern image taking laser beam, the laser microscope (camera) 7 receives reflected light from the semiconductor wafer 2 and obtains a wafer pattern image.

Next, an analysis method using the semiconductor analysis apparatus described above will be described.

First, a semiconductor wafer 2 that is an object to be analyzed is placed on the stage 3. By using a measuring apparatus similar to a semiconductor wafer prober, its probes are pressed against the bonding pads for electrical connection. Then, operation voltages and input signals that operate the internal circuits are supplied through the probes from a tester that is composed of a pattern generation circuit, an oscillation circuit and a control circuit, to thereby place the internal circuits in an operating state.

Next, the Raman laser beam and wafer pattern image taking laser beam emitted from the laser oscillator 1 are irradiated on the surface of the semiconductor wafer 2. The Raman spectroscopy apparatus 4 takes out light (scattered light) scattered in the solid of the semiconductor wafer 2, and the Raman spectroscopy apparatus 4 spectroscopically separates the light, whose frequency is converted by the data converter 5 into light intensity, which is then inputted in the computer 6 to calculate peak values. At the same time, the laser microscope 7 receives light (reflected light) reflected on the surface of the semiconductor wafer 2 to obtain a pattern image. Then, the data converter 8 converts data representative of the pattern image, and the converted data is inputted in the computer 6.

Next, the computer 6 calculates amounts of shifts in Raman spectra, which appear due to the Raman effect, whereby temperature of minute areas of the object to be measured is calculated based on the relation between the temperature obtained in advance and the amounts of frequency shifts. Then, the temperature data for the fine regions and the pattern image data are combined, and the same is outputted.

In other words, when current is circulated through devices on a wafer or in the state of chips, and if defective locations such as metal short-circuits are present, heat is generated at the defective locations. The semiconductor analysis apparatus described above uses Raman spectra shifts given by a Raman spectroscopy apparatus to detects location where heat is generated, whereby minute defective locations in minute areas can be accurately specified.

In the embodiment described above, Raman spectra shifts are used to detect heat generated at defective locations to thereby specify the defective locations. With this Raman spectroscopic analysis, Raman spectrum shifts are sensitive to temperatures of an object to be measured. Therefore, it can specify a defective location such as a subtle metal short-circuit defect to a degree that can be barely specified by a SEM, and is capable of analyzing a spot region of up to 0.2 µm. Therefore, a defective area such as a metal short-circuit can be narrowed down to a fine region in a short time. In particular, defective locations can be readily and accurately specified even when miniaturization of the design rule is further advanced.

Also, unlike the conventional technology, the present embodiment does not use liquid crystal that is harmful to the human body, and therefore safety of the operators can be expected.

It is noted that the present invention is not limited to the embodiment described above, but many modifications thereof can be implemented.

As described above, the present invention uses Raman spectra shifts to detect heat generated at defective locations to thereby specify the defective locations. Accordingly, the present invention can provide a semiconductor analysis apparatus, a semiconductor analysis method and a method for manufacturing a semiconductor device, in which a minute defective location can be accurately determined.

The entire disclosure of Japanese Patent Application No. 2001-194429 filed Jun. 27, 2001 is incorporated by reference.

What is claimed is:

1. A semiconductor analysis apparatus comprising:

a laser oscillator that emits a Raman laser beam and a pattern taking laser beam for taking a pattern image of an object to be measured;

a stage for mounting an object to be measured onto which the Raman laser beam and the pattern taking laser emitted from the laser oscillator are irradiated;

a Raman spectroscopy apparatus that takes out to spectroscopically separate scattered light from the object to be measured onto which the Raman laser beam is irradiated, and detects Raman spectra obtained;

a camera that receives reflected light from the object to be measured onto which the pattern taking laser beam is irradiated to obtain a pattern image of the object to be measured; and a computer that combines data of the Raman spectra detected by the Raman spectroscopy apparatus and data of the pattern image obtained by the camera, to thereby judge a temperature of a fine region in the pattern of the object to be measured.

* * * * *